US008058047B2

(12) United States Patent
Tzortzis et al.

(10) Patent No.: US 8,058,047 B2
(45) Date of Patent: Nov. 15, 2011

(54) α-GALACTOSIDASE WITH TRANSGALACTOSYLATING ACTIVITY

(75) Inventors: Georgios Tzortzis, Reading (GB);
Athanasios K Goulas, Reading (GB);
Theodoros Goulas, Reading (GB)

(73) Assignee: Clasado, Inc., Apartado (PA)

( * ) Notice: Subject to any disclaimer, the term of this patent is extended or adjusted under 35 U.S.C. 154(b) by 338 days.

(21) Appl. No.: 12/086,834

(22) PCT Filed: Dec. 19, 2006

(86) PCT No.: PCT/GB2006/004796
§ 371 (c)(1),
(2), (4) Date: Aug. 7, 2008

(87) PCT Pub. No.: WO2007/071987
PCT Pub. Date: Jun. 28, 2007

(65) Prior Publication Data
US 2009/0285933 A1 Nov. 19, 2009

(30) Foreign Application Priority Data
Dec. 20, 2005 (GB) .................................. 0525857.9

(51) Int. Cl.
*C12N 9/40* (2006.01)
*C12Q 1/44* (2006.01)
*C07K 14/00* (2006.01)
(52) U.S. Cl. ........................... 435/208; 435/19; 530/350
(58) Field of Classification Search .................. 435/208, 435/19; 530/350
See application file for complete search history.

(56) References Cited

U.S. PATENT DOCUMENTS

| | | | |
|---|---|---|---|
| 4,435,389 A | | 3/1984 | Mutai et al. |
| 4,944,952 A | | 7/1990 | Kobayashi et al. |
| 5,149,640 A | | 9/1992 | Oonishi et al. |
| 5,294,546 A | | 3/1994 | Dombou et al. |
| 7,794,746 B2 | * | 9/2010 | Gibson et al. ................. 424/439 |
| 2002/0086358 A1 | | 7/2002 | Jorgensen et al. |
| 2007/0274955 A1 | * | 11/2007 | Gibson et al. ................. 424/93.4 |
| 2009/0110770 A1 | * | 4/2009 | Tzortzis et al. ................. 426/7 |
| 2009/0117080 A1 | * | 5/2009 | Tzortzis et al. .............. 424/93.2 |
| 2009/0155860 A1 | * | 6/2009 | Goulas et al. ................. 435/101 |
| 2011/0082102 A1 | * | 4/2011 | Tzortzis et al. ................. 514/53 |

FOREIGN PATENT DOCUMENTS

| | | |
|---|---|---|
| EP | 0 438 182 A1 | 7/1991 |
| EP | 1 227 152 A1 | 7/2002 |
| GB | 2 412 380 B | 11/2005 |
| JP | 62059290 | 3/1987 |
| JP | 3049692 | 3/1991 |
| JP | 3049693 | 3/1991 |
| JP | 3246296 | 11/1991 |
| JP | 5-146273 | 6/1993 |
| JP | 5-146296 | 6/1993 |
| JP | 7089976 | 4/1995 |
| JP | 9121853 | 5/1997 |
| JP | 10023898 | 1/1998 |
| WO | WO 88/08025 | 10/1988 |
| WO | WO 96/06924 | 3/1996 |
| WO | WO 00/33854 | 6/2000 |
| WO | WO 00/46345 | 8/2000 |
| WO | WO 01/90317 A2 | 11/2001 |
| WO | WO 2004/074496 A1 | 9/2004 |
| WO | WO 2005/003329 A1 | 1/2005 |
| WO | WO 2007/054459 A2 | 5/2007 |

OTHER PUBLICATIONS

Smeianov et al., GenBank accession No. AAG02023, 2000.*
Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Smeianov et al., GenBank accession No. AF160969, 2000.*
Database UniProt [Online] Nov. 1, 1999, "Alpha-galactosidase (EC 3.2.1.22)." retrieved from EBI accession No. UNIPROT:Q9XCX2; Database accession No. Q9XCX2.
Database Geneseq [Online] Nov. 19, 2002, "Bifidobacterium longum NCC2705 ORF amino acid sequence SEQ ID No. 919." retrieved from EBI accession No. GSP:ABP66175; Database accession No. ABP66175.
Database UniProt [Online] Sep. 27, 2005, "Glycoside hydrolase, clan GH-D." retrieved from EBI accession No. UNIPROT:Q40Z83; Database accession No. Q40Z83.
Database UniProt [Online] Dec. 20, 2005, "Alpha-galactosidase (EC 3.2.1.22)." retrieved from EBI accession No. UNIPROT:Q2XQ11; Database accession No. Q2XQ11.
Database UniProt [Online] May 30, 2006, "Alpha-galactosidase (EC 3.2.1.22)." retrieved from EBI accession No. UNIPROT:Q1KTD9; Database accession No. Q1KTD9.
George Tzortzis et al: "Synthesis of prebiotic galactooligosaccharides using whole cells of a novel strain, *Bifidobacterium bifidum* NCIMB 41171" Applied Microbiology and Biotechnology, Springer-Verlag, BE, vol. 68, No. 3, Aug. 1, 2005, pp. 412-416, ISSN: 1432-0614.
Goulas A et al: "Development of a process for the production and purification of α- and β-galactooligosaccharides from *Bifidobacterium bifidum* NCIMB 41171" International Dairy Journal, vol. 17, No. 6, Jun. 2007, pp. 648-656.
Lamoureux L et al: "Production of Oligosaccharides in Yogurt Containing Bifidobacteria and Yogurt Cultures" Journal of Dairy Science, American Dairy Science Association, Savoy, IL, US, vol. 85, No. 5, May 2002, pp. 1058-1069, ISSN: 0022-0302 the whole document, in particular Table 5.
Scalabrini P et al: "Characterization of Bifidobacterium Strains for Use in Soymilk Fermentation" International Journal of Food Microbiology, Elsevier Science Publishers, Amsterdam, NL, vol. 39, No. 3, 1998, pp. 213-219, ISSN: 0168-1605 the whole document, in particular Table 1.

(Continued)

*Primary Examiner* — Delia Ramirez
(74) *Attorney, Agent, or Firm* — Christie, Parker & Hale, LLP

(57) ABSTRACT

The present invention concerns a new α-galactosidase with transgalactosylating activity isolated from *Bifidobacterium bifidum*. The α-galactosidase is capable of converting mellibiose to α-galactobiose disaccharides which may be incorporated into numerous food products or animal feeds for improving gut health by promoting the growth of bifidobacteria in the gut, and repressing the growth of the pathogenic microflora.

4 Claims, 6 Drawing Sheets

OTHER PUBLICATIONS

Van Den Broek L A M et al: "Synthesis of alpha-galacto-oligosaccharides by a cloned alpha-galactosidase from *Bifidobacterium adolescentis*" Biotechnology Letters, vol. 21, No. 5, May 1999, pp. 441-445, ISSN: 0141-5492.

Van Laere K M J et al: "Transglycosidase activity of *Bifidobacterium adolescentis* DSM 20083 alpha-galactosidase" Applied Microbiology and Biotechnology, Springer Verlag, Berlin, DE, vol. 52, No. 5, Nov. 1999 pp. 681-688, ISSN: 0175-7598.

Chabaud, et al., "*Contribution of Interleukin 17 to Synovium Matrix Destruction in Rheumatoid Arthritis*", Cytokine, vol. 12, No. 7, Jul. 2000, pp. 1092-1099.

Palframan, et al., "*Carbohydrate Preferences of Bifidobacterium Species Isolated from the Human Gut*", Current Issues in Intestinal Microbiology, vol. 4, 2003, pp. 71-75.

Yuan, et al., "*Feruloyl oligosaccharides stimulate the growth of Bifidobacterium bifidum*", Anaerobe, vol. 11, 2005, pp. 225-229.

Lawson, Paul A., et al., "Recognition of *Fusobacterium nucleatum* subgroups Fn-1, Fn-2 and Fn-3 by ribosomal RNA gene restriction patterns"; FEMS Microbiology Letters 65 (1989) pp. 41-46.

Hanatani, Mitsuya et al., "Physical and Genetic Characterization of the Melibiose Operon and Identification of the Gene Products in *Escherichia coli*"; The Journal of Biological Chemistry, Feb. 10, 1984, vol. 259, No. 3, pp. 1807-1812.

Karlsson, Karl-Anders, "Animal Glycosphingolipids as Membrane Attachment Sites for Bacteria", Annu. Rev. Biochem., 1989, 58:309-50.

Paton, James C., et al., "Pathogenesis and Diagnosis of Shiga Toxin-Producing *Escherichia coli* Infections", Clinical Microbiology Reviews, Jul. 1998, pp. 450-479.

Møller, Peter L., et al., Intra- and Extracellular β-Galactosidases from *Bifidobacterium bifidum* and *B. infantis*: Molecular Cloning, Heterologous Expression, and Comparative Characterization, Applied and Environmental Microbiology, May 2001, pp. 2276-2283.

Sambrook J. Molecular Cloning: A Laboratory Manual (2002).

International Preliminary Examination Report, dated Jul. 3, 2008, for International Patent Application No. PCT/GB2006/004796.

Albersheim, et al., "*A Method for the Analysis of Sugars in Plant Cell-Wall Polysaccharides by Gas-Liquid Chromatography*", Carbohydrate Research, 5, 1967, pp. 340-345.

Blakeney, A.,et al., "*A Simple and Rapid Preparation of Alditol Acetates for Monosaccharide Analysis*", Carbohydrate Research, Elsevier Scientific Publishing Co., vol. 113 (1983) pp. 291-299.

Blanchette, D., et al., "α- and β-*Galactosidase properites of Bifidobacterium infantis*", Milchwissenschaft, vol. 47, No. 1, (1992), pp. 18-21.

Dumortier, V., et al., "*Primary Structure of Ten Galactosides formed by Transglycosylation During Lactose Hydrolysis by Bifidobacterium bifidum*", Carbohydrate Research, vol. 201, 1990 pp. 115-123.

Carpita, N., et al., "*Linkage Structure of Carbohydrates by Gas Chromatography-Mass Spectrometry (GC-MS) of Partially Methylated Alditol Acetates*", Analysis of Carbohydrates by GLC and MS, pp. 157-216, 1989.

Ciucanu, I., et al., "*A Simple and Rapid Method for the Permethylation of Carbohydrates*", Carbohydrate Research, 131 (1984) pp. 209-217, Elsevier Science Publishers.

Crittenden; R., "*Prebiotics*"; Probiotics: A Critical Review ISBN 1-898486-15-8; 1999 Horizon Scientific Press, Wymondham, U.K., pp. 141-156.

Database EMBL (Online) Oct. 26, 2000, "*Bifidobacterium bifidum* gene for beta-galactosidase (3701 bp)" 3 pages.

Database UniProt (Online) Mar. 1, 2001, "Beta-galactosidase (EC 3.2.1.23)." 1 page.

Database EMBL (Online) Aug. 24, 2004, "*Bifidobacterium breve* B-galactosidase (B-gal) gene, complete cds" 2 pages.

Doares, Steven, et al., "*An Improved Method for the Preparation of Standards for Glycosyl-linkage Analysis of Complex Carbohydrates*", Carbohydrate Research, 210 (1991) pp. 311-317, Elsevier Science Publishers.

Dumortier, V., et al; "*Purification and properties of a β-D-galactosidase from Bifidobacterium bifidum exhibiting a transgalactosylation reaction*"; Biotechnol. Appl. Biochem. 19, pp. 341-354 (1994).

Gibson, G., et al., "*Dietary Modulation of the Human Colonic Microbiota: Introducing the Concept of Prebiotics*", Critical Review, American Institute of Nutrition, 1995, pp. 1401-1412.

Gibson; G. "*Bifidobacteria and Oligosaccharides—The Functional Use of Prebiotics*"; Positive Nutrition: Functional Foods; IBC Technical Services, London 1995, 34 pages.

Gibson; G., "*Prebiotics: New Developments in Functional Foods*"; Chandos Publishing, Oxford 2000, 96 pages.

Gopal, P.K., et al., "*Utilisation of galacto-oligosaccharides as selective substrates for growth by lactic acid bacteria including Bifidobacterium lactis DR 10 and Lactobacillus rhamnosus DR20*," International Dairy Journal 11 (2001) pp. 19-25.

Hashimoto, H., et al., "*Production of the Positional Isomers of α-Galactobiose by the Reverse Reaction of α-Galactosidase Candida guilliermondii H-404*", Journal of Applied Glycoscience, vol. 48, No. 3, (2001), pp. 279-285.

Hashimoto, H., et al., "*Candida guilliermondii H-404*", Journal of Applied Glycoscience, vol. 41, No. 2, (1994), pp. 143-150 (includes English abstract).

Hung et al., "*Molecular and Biochemical Analysis of Two Beta-Galactosidases from Bifidobacterium Infantis, HL96, Appln Environ Microbiol.* 67(9)"4256-63, 2001.

Ito, et al.; "*Effects of Administration of Galactooligosaccharides on the Human Faecal Microflora, Stool Weight and Abdominal Sensation*"; Microbial Ecology in Health and Disease, vol. 3:285-292 (1990).

Ito, et al.; "*Effects of Transgalactosylated Disaccharides on the Human Intestinal Microflora and Their Metabolism*"; J. Nutr. Sci. Vitaminol., 39, 279-288, 1993.

Krieg, P.A., et al.; "In Vitro RNA Synthesis with SP6 RNA Polymerase", Methods in Enzymology, 1987, vol. 155, pp. 397-415.

MacCormick, C.A., et al., "*Characterization of a Variant of the Polysaccharide Acetan Produced by a Mutant of Acetobacter Xylinum Strain CR1/4*", Journal of AppliedBacteriology 1993, 74, pp. 196-199.

MacFarlane, G., et al., "*Validation of a Three-Stage Compound Continuous Culture System for Investigating the Effect of Retention Time on the Ecology and Metabolism of Bacteria in the Human Colon*", Microbial Ecology, 1998, 35:180-187.

Matsumoto et al., "*Galactooligosaccharides*", Japanese Technology Reviews, Section E, Chapter 5, vol. 2.3, 1993, pp. 90-94 (9 sheets).

Olano-Martin, E., et al; "*Pectins and Pectic-oligosaccharides inhibit Escherichia coli O157:H7 Shiga toxin as directed towards the human colonic cell line HT29*"; FEMS Microbiology Letters 218 (2003), pp. 101-105.

Onishi, N., et al; "*Production of Galacto-Oligosaccharide from Lactose by Sterigmatomyces elviae CBS8119*", Applied and Environmental Microbiology, Nov. 1995, pp. 4022-4025.

Prenosil, J.E., et al; "*Formation of Oligosaccharides during Enzymatic Lactose: Part 1: State of Art*"; Biotechnology and Bioengineering, vol. 30, pp. 1019-1025 (1987).

Rabiu, B., et al; "*Synthesis and Fermentation Properties and Novel Galacto-Oligosaccharides by β-Galactosidases from Bifidobacterium Species*"; Applied and Environmental Microbiology, Jun. 2001, pp. 2526-2530.

Rowland et al., "*The effects of transgalactosylated oligosaccharides on gut flora metabolism in rats associated with a human faecal microflora*", Journal of Applied Bacteriology, 1993, 74, pp. 667-674.

Russel P., 2002 iGenetics, Pearson Education, Inc., San Francisco, pp. 187-189.

Sako, T., et al; "*Recent progress on research and applications of non-digestible galacto-oligosaccharides*"; International Dairy Journal 9 (1999), pp. 69-80.

Schell, et al., "*The genome sequence of Bifidobacterium longum reflects its adaptation to the human gastrointestinal tract*", Proceedings of the National Academy of Science, vol. 99, Oct. 29, 2009, pp. 14422-14427 (including PNAS Corrections, Jun. 28, 2005, pp. 9429-9430).

Sweet, David, et al., "*Quantitative Analysis by Various G.L.C. Response-Factor Theories for Partially Methylated and Partially*

*Ethylated Alditol Acetates, Carbohydrate Research*", 40 (1975) pp. 217-225, Elsevier Science Publishers.

Tanaka, R., et al; "Effects of Administration of TOS and Bifidobacterium breve 4006 on the Human Fecal Flora"; *Bifidobacteria Microflora*, vol. 2(1), 17-24, 1983.

Van Laere K, M J, et al: "*Transglycosidase activity of Bifidobacterium adolescentis DSM 20083 alpha-galactosidase*" Applied Microbiology and Biotechnology, Springer Verlag, Berlin, DE, vol. 52, No. 5, Nov. 1999 pp. 681-688, ISSN: 0175-7598 the whole document.

Van Laere, K.,et al; "*Characterization of a Novel β-Galactosidase from Bifidobacterium adolescentis DSM 20083 Active towards Transgalactooligosaccharides*", Applied and Environmental Microbiology, Apr. 2000, pp. 1379-1384.

Zarate, S., et al; "*Oligosaccharide Formation During Enzymatic Lactose Hydrolysis: A Literature Review*"; Journal of Food Protection, vol. 53, No. 3, pp. 262-268 (Mar. 1990).

Ziggers, D., "*TOS, a new prebiotic derived from whey,*" Feed Mix, vol. 9, No. 6, 2001, pp. 7-9.

International Search Report for PCT/GB2004/002815 dated Jul. 12, 2004.

International Search Report, dated Jul. 4, 2007, corresponding to PCT/GB2007/001081.

Written Opinion of the International Searching Authority, dated Jul. 4, 2007, corresponding to PCT/GB2007/001081.

International Search Report dated Jun. 11, 2007, corresponding to PCT/GB2006/004796.

International Preliminary Report on Patentability and Written Opinion of the International Searching Authority dated Oct. 9, 2008, for corresponding International application No. PCT/GB2007/001081.

International Search Report, dated May 14, 2007, corresponding to PCT/GB2007/000178.

Written Opinion of the International Searching Authority, dated May 14, 2007, corresponding to PCT/GB2007/000178.

Japanese Office Action dated Dec. 9, 2008, in corresponding Japanese Patent Application No. 2006-500267, along with English translation.

U.S. Office Action dated Sep. 8, 2010 for U.S. Appl. No. 12/225,626.

U.S. Office Action dated Oct. 6, 2009 for U.S. Appl. No. 10/552,483.

U.S. Notice of Allowance dated Oct. 28, 2010 for U.S. Appl. No. 10/552,483.

U.S. Office action dated Dec. 6, 2010 for U.S. Appl. No. 12/223,508.

International Search Report and Written Opinion dated May 18, 2007 for International Application No. PCT/EP2006/068029 (9 sheets).

International Preliminary Report on Patentability dated May 14, 2008 for International Application No. PCT/EP2006/068029 (7 sheets).

U.S. Office Action dated Feb. 15, 2011 for U.S. Appl. No. 12/084,681 (27 sheets).

International Search Report dated Sep. 4, 2009 for International Application No. PCT/GB2009/001302 (3 sheets).

An, et al, "*Isolation of Phaffia rhodozyma Mutants with Increased Astaxanthin Content*", Applied and Environmental Microbiology, vol. 55, No. 1, Jan. 1989, pp. 116-124.

U.S. Notice of Allowance dated May 27, 2011 for U.S. Appl. No. 12/223,508 (8 sheets).

U.S. Office Action dated Jun. 3, 2011 for U.S. Appl. No. 12/225,626 (8 sheets).

* cited by examiner

Figure 1.

```
   1 taaaccttca taaaaggaaa caaaagctgg aagctccacc gcggtggcgg ccgctctaga
  61 actagtggat cccccgggct gcagctcgtg gtgatctacg ttccgttcct caactccgcg
 121 ttcggcacca cgccgctcgg accgtgggca tgggtcgagt gcatctgcct cgccgcggtc
 181 gtactgatcg cctcggaaat ctacaaggcg atcatgcgcg ccatcgaccg caagcgcggc
 241 atcatggcat aacaatgcca taagcctcca ccggcagtca gggctcccgc tctccacatc
 301 ggaaaacggg agcccttctc atacccggga atcgctgaat atgcggtgac atgacggaac
 361 gatgtcgtag catcggaggc gaaccatata tcaatggcac gttccgaagg gattcgcaat
 421 gtcactcatc gaacaattcc atggcgcgc cgccgatgga acggaactca ccgctattta
 481 tgctgagcag ccggctgctg atgtggcgtt cgcgctggtc ttcgccggtc acggtcttcc
 541 gcgcttcgtg cactgggcc gaccgctcgc ggcgccggga accgtactcg ccgcatacga
 601 cgccctgcgg ccgcagcgcg tgtccggcgc gctggacgag accgcctggc aagcatcat
 661 gcccacgcaa agcgagtcgt ggatagggc accgcgactg gatatccggc gcgccggcgt
 721 aacgccgttc tgtgcattca cggtgaccgg catcgcaatc cgtcaggacg aacgccaagg
 781 cgttgacgtg tctgacggcg tggacggtgc cgcgcatacc gtcacgcaac aggtgccggt
 841 cgtcaccgtg accgcgtcgg atgccgagca gggcgtggaa ctgtcatgga cggccgaact
 901 gttgcccggc ggactgatca gacagcgcac cacgctgcgt aatcttccag ccggtaatct
 961 tccgaccggt gacttggaag tcggtaaagt cgaactcggc ttcccgctcc cggcacttgc
1021 cacggagata ctcaccacca ccggccatca tctgcgcgaa cgcagcccgc agcggcagcc
1081 gctgaccgaa ggacgcttcg agaaggtctc gatggcgggg cgcccaggtt ttgacgcctc
1141 tctgttgctt tccgcgggcg agcccggctt cgggttcgag catggcgagg tctattcggt
1201 gcatgtgggc tggagcggca attccgtgct gtcggcagag cgtcagccgt atacgaccgg
1261 tctgattggc ggcggcgagg tgctgctcgg cggcgaggcc acgctcgccc gcggcgaaac
1321 gtacaccacc ccgtggctgt acgggtcgta cggtgacggg ctcaacgagg tggctgcgag
1381 attccatgat tacgtacgct cctgtcaccc ggatcgcc gtcaagccgc gtccggtgat
1441 tctcaacacg tgggaggccg tgtatttcga ccatgactac gacacgttga aggctctggc
1501 cgataaggcc ggggattccg gtgtcgaacg gttcgtggtg gatgacggct ggttcggctc
1561 ccgccgagac tccacatccg ggctcggcga ctggcaaata gcgcaggatg tgtggccgga
1621 cgggccgaag agcctcaagg cgctcgccga ttacgtgcac ggaaaaggca tggagttcgg
1681 cctgtggttc gaaccggaga tggtcaaccc ggattccgac gtggcccgcg cccaccctga
1741 ctgggtgctg cgcccgactg cgaaccgtct gccgatgcag ggacgctcgc agcaagtgct
1801 cgacctgacc aatcccgacg cctaccgata catccatgat tccatcgatg cgctggtcgg
1861 cgagttgggc atcgactaca tcaaatggga ccacaacaaa ttcgtcaccg aggcggtctc
1921 gccacgtacc ggcaggccgg cggtgcacgg gcagacgctc gccgtgtacc ggatgttccg
1981 tgacctcgaa gtcgcgcatc cgggactgga gattgagagt tgcgcatcgg gcggcggccg
2041 tatcgacctg ggcatactcg aattcgccag ccgcgtgtgg acgtccgact gcgtggaccc
2101 ggtcgaggcg gccgatattc agcggtacac gtcgctgctc gtgccgcccc gcatgatggg
2161 cgagcatgtg gggggcgagtc ctgcacattc cacgcatcgc gccacgagcc aggagatgcg
2221 catggcgatg gcgttcttcg ggcacatggg cgtcgaatgg aatctgctca aggagccgga
2281 cgaggcgttg aacaagctcg gcgaatgggt cgccgaatac aagaggcacc gcgcatggtt
2341 cgcgatcgac acgtgcgtgc acgccgatat cgccgatccg gccgtccggg tgacggcat
2401 ggtcaagccg gatcgttccg cggcgttcta ccggttcacg caactgacaa cgtcccagac
2461 tctccctgcg gcgccgattc gcgtgcccgg tcttgacccc gatggcacgt accgcataca
2521 gccgttgtgg ctggatctcg atctcgacgg gcttggtctt ggcagcggcc agtcgccgtt
2581 gggctggtgg accaaagacg cgtgctgat gacgggccgg gcgctgatga cctacgggtt
2641 gcgccctcca tcgctgcatc cggcgcagtc ggtgctgttc accgccattc gccaataagc
2701 cagacggcat cgaacggagc ataacaatgt gccggcggcc cagtcatgga gtcgccggca
2761 cattgcgtca aagaacttgg gtatcggctc tagtcgttga cgtcggcctt gtagaagttc
2821 acgtaggaac ggctggggt cgggccgcgc tggccctgat aatgggagcc ggtgcccttg
2881 gagccgtaag ggtgctcggc cggagagctg agctggaaga agcacatctg cccgatcttc
2941 atgccgggcc agagcttgac cggaagcgtc gacacgttgc tcaactccag cgtgatatgc
3001 ccctcgaaac cggggtcgat gaagccggcc gtcgaatgtg tgaggatgcc cagacggccc
3061 agcgagcttt tgccttccaa gcgtgccgcc accgtcgcgt cgagcttgac ggtactcccc
3121 acgtcgagc
```

Figure 2.

```
 421 atgtcactcatcgaacaattccatggcgccgccgccgatggaacg
      M  S  L  I  E  Q  F  H  G  A  A  A  D  G  T
 466 gaactcaccgctatttatgctgagcagccggctgctgatgtggcg
      E  L  T  A  I  Y  A  E  Q  P  A  A  D  V  A
 511 ttcgcgctggtcttcgccggtcacggtcttccgcgcttcgtgcac
      F  A  L  V  F  A  G  H  G  L  P  R  F  V  H
 556 tggggccgaccgctcgcggcgccgggaaccgtactcgccgcatac
      W  G  R  P  L  A  A  P  G  T  V  L  A  A  Y
 601 gacgccctgcggccgcagcgcgtgtccggcgcgctggacgagacc
      D  A  L  R  P  Q  R  V  S  G  A  L  D  E  T
 646 gcctggccaagcatcatgcccacgcaaagcgagtcgtggataggg
      A  W  P  S  I  M  P  T  Q  S  E  S  W  I  G
 691 gcaccgcgactggatatccggcgcgccggcgtaacgccgttctgt
      A  P  R  L  D  I  R  R  A  G  V  T  P  F  C
 736 gcattcacggtgaccggcatcgcaatccgtcaggacgaacgccaa
      A  F  T  V  T  G  I  A  I  R  Q  D  E  R  Q
 781 ggcgttgacgtgtctgacggcgtggacggtgccgcgcataccgtc
      G  V  D  V  S  D  G  V  D  G  A  A  H  T  V
 826 acgcaacaggtgccggtcgtcaccgtgaccgcgtcggatgccgag
      T  Q  V  P  V  V  T  V  T  A  S  D  A  E
 871 cagggcgtggaactgtcatggacggccgaactgttgcccggcgga
      Q  G  V  E  L  S  W  T  A  E  L  L  P  G  G
 916 ctgatcagacagcgcaccacgctgcgtaatcttccagccggtaat
      L  I  R  Q  R  T  T  L  R  N  L  P  A  G  N
 961 cttccgaccggtgacttggaagtcggtaaagtcgaactcggcttc
      L  P  T  G  D  L  E  V  G  K  V  E  L  G  F
1006 ccgctcccggcacttgccacggagatactcaccaccaccggccat
      P  L  P  A  L  A  T  E  I  L  T  T  T  G  H
1051 catctgcgcgaacgcagcccgcagcggcagccgctgaccgaagga
      H  L  R  E  R  S  P  Q  R  Q  P  L  T  E  G
1096 cgcttcgagaaggtctcgatggcggggcgcccaggttttgacgcc
      R  F  E  K  V  S  M  A  G  R  P  G  F  D  A
1141 tctctgttgctttccgcgggcgagcccggcttcgggttcgagcat
      S  L  L  S  A  G  E  P  G  F  G  F  E  H
1186 ggcgaggtctattcggtgcatgtgggctggagcggcaattccgtg
      G  E  V  Y  S  V  H  V  G  W  S  G  N  S  V
1231 ctgtcggcagagcgtcagccgtatacgaccggtctgattggcggc
      L  S  A  E  R  Q  P  Y  T  T  G  L  I  G  G
1276 ggcgaggtgctgctcggcggcgaggccacgctcgcccgcggcgaa
      G  E  V  L  L  G  G  E  A  T  L  A  R  G  E
1321 acgtacaccaccccgtggctgtacgggtcgtacggtgacgggctc
      T  Y  T  T  P  W  L  Y  G  S  Y  G  D  G  L
1366 aacgaggtggctgcgagattccatgattacgtacgctcctgtcac
      N  E  V  A  A  R  F  H  D  Y  V  R  S  C  H
1411 ccggatctcgccgtcaagccgcgtccggtgattctcaacacgtgg
      P  D  L  A  V  K  P  R  P  V  I  L  N  T  W
1456 gaggccgtgtatttcgaccatgactacgacacgttgaaggctctg
      E  A  V  Y  F  D  H  D  Y  D  T  L  K  A  L
1501 gccgataaggccggggattccggtgtcgaacggttcgtggtggat
      A  D  K  A  G  D  S  G  V  E  R  F  V  V  D
1546 gacggctggttcggctcccgccgagactccacatccgggctcggc
      D  G  W  F  G  S  R  R  D  S  T  S  G  L  G
1591 gactggcaaatagcgcaggatgtgtggccggacgggccgaagagc
```

Figure 2 (continuation)

```
                D   W   Q   I   A   Q   D   V   W   P   D   G   P   K   S
1636   ctcaaggcgctcgccgattacgtgcacggaaaaggcatggagttc
        L   K   A   L   A   D   Y   V   H   G   K   G   M   E   F
1681   ggcctgtggttcgaaccggagatggtcaacccggattccgacgtg
        G   L   W   F   E   P   E   M   V   N   P   D   S   D   V
1726   gcccgcgcccaccctgactgggtgctgcgcccgactgcgaaccgt
        A   R   A   H   P   D   W   V   L   R   P   T   A   N   R
1771   ctgccgatgcagggacgctcgcagcaagtgctcgacctgaccaat
        L   P   M   Q   G   R   S   Q   Q   V   L   D   L   T   N
1816   cccgacgcctaccgatacatccatgattccatcgatgcgctggtc
        P   D   A   Y   R   Y   I   H   D   S   I   D   A   L   V
1861   ggcgagttgggcatcgactacatcaaatgggaccacaacaaattc
        G   E   L   G   I   D   Y   I   K   W   D   H   N   K   F
1906   gtcaccgaggcggtctcgccacgtaccggcaggccggcggtgcac
        V   T   E   A   V   S   P   R   T   G   R   P   A   V   H
1951   gggcagacgctcgccgtgtaccggatgttccgtgacctcgaagtc
        G   Q   T   L   A   V   Y   R   M   F   R   D   L   E   V
1996   gcgcatccgggactggagattgagagttgcgcatcgggcggcggc
        A   H   P   G   L   E   I   E   S   C   A   S   G   G   G
2041   cgtatcgacctgggcatactcgaattcgccagccgcgtgtggacg
        R   I   D   L   G   I   L   E   F   A   S   R   V   W   T
2086   tccgactgcgtggacccggtcgagcgggccgatattcagcggtac
        S   D   C   V   D   P   V   E   R   A   D   I   Q   R   Y
2131   acgtcgctgctcgtgccgccctgcatgatgggcgagcatgtgggg
        T   S   L   L   V   P   P   C   M   M   G   E   H   V   G
2176   gcgagtcctgcacattccacgcatcgcgccacgagccaggagatg
        A   S   P   A   H   S   T   H   R   A   T   S   Q   E   M
2221   cgcatggcgatggcgttcttcgggcacatgggcgtcgaatggaat
        R   M   A   M   A   F   F   G   H   M   G   V   E   W   N
2266   ctgctcaaggagccggacgaggcgttgaacaagctcggcgaatgg
        L   L   K   E   P   D   E   A   L   N   K   L   G   E   W
2311   gtcgccgaatacaagaggcaccgcgcatggttcgcgatcgacacg
        V   A   E   Y   K   R   H   R   A   W   F   A   I   D   T
2356   tgcgtgcacgccgatatcgccgatccggccgtccgggtcgacggc
        C   V   H   A   D   I   A   D   P   A   V   R   V   D   G
2401   atggtcaagccggatcgttccgcggcgttctaccggttcacgcaa
        M   V   K   P   D   R   S   A   A   F   Y   R   F   T   Q
2446   ctgacaacgtcccagactctccctgcggcgccgattcgcgtgccc
        L   T   T   S   Q   T   L   P   A   A   P   I   R   V   P
2491   ggtcttgaccccgatggcacgtaccgcatacagccgttgtggctg
        G   L   D   P   D   G   T   Y   R   I   Q   P   L   W   L
2536   gatctcgatctcgacgggcttggtcttggcagcggccagtcgccg
        D   L   D   L   D   G   L   G   L   G   S   G   Q   S   P
2581   ttgggctggtggaccaaagacggcgtgctgatgacgggccgggcg
        L   G   W   W   T   K   D   G   V   L   M   T   G   R   A
2626   ctgatgacctacgggttgcgcctccatcgctgcatccggcgcag
        L   M   T   Y   G   L   R   P   P   S   L   H   P   A   Q
2671   tcggtgctgttcaccgccattcgccaataa   2700
        S   V   L   F   T   A   I   R   Q   *
```

Figure 3.

MSLIEQFHGAAADGTELTAIYAEQPAADVAFALVFAGHGLPRFV
HWGRPLAAPGTVLAAYDALRPQRVSGALDETAWPSIMPTQSESWIGAPRLDIRRAGVTPFCAFTVTG
IAIRQDERQGVDVSDGVDGAAHTVTQQVPVVTVTASDAEQGVELSWTAELLPGGLIRQRTTLRNLP
AGNLPTGDLEVGKVELGFPLPALATEILTTTGHHLRERSPQRQPLTEGRFEKVSMAGRPGFDASLLLS
AGEPGFGFEHGEVYSVHVGWSGNSVLSAERQPYTTGLIGGGEVLLGGEATLARGETYTTPWLYGSY
GDGLNEVAARFHDYVRSCHPDLAVKPRPVILNTWEAVYFDHDYDTLKALADKAGDSGVERFVVDD
GWFGSRRDSTSGLGDWQIAQDVWPDGPKSLKALADYVHGKGMEFGLWFEPEMVNPDSDVARAHP
DWVLRPTANRLPMQGRSQQVLDLTNPDAYRYIHDSIDALVGELGIDYIKWDHNKFVTEAVSPRTGR
PAVHGQTLAVYRMFRDLEVAHPGLEIESCASGGG

SEQUENCE LISTING

<160> NUMBER OF SEQ ID NOS: 2

<210> SEQ ID NO 1
<211> LENGTH: 3129
<212> TYPE: DNA
<213> ORGANISM: Bifidobacterium bifidum
<220> FEATURE:
<221> NAME/KEY: gene
<222> LOCATION: (1)..(6)

<400> SEQUENCE: 1

```
taaaccttca taaaaggaaa caaaagctgg aagctccacc gcggtggcgg ccgctctaga      60
actagtggat cccccgggct gcagctcgtg gtgatctacg ttccgttcct caactccgcg     120
ttcggcacca cgccgctcgg accgtgggca tgggtcgagt gcatctgcct cgccgcggtc     180
gtactgatcg cctcggaaat ctacaaggcg atcatgcgcg ccatcgaccg caagcgcggc     240
atcatggcat aacaatgcca taagcctcca ccggcagtca gggctcccgc tctccacatc     300
ggaaaacggg agcccttctc ataccccgga atcgctgaat atgcggtgac atgacggaac     360
gatgtcgtag catcggaggc gaaccatata tcaatggcac gttccgaagg gattcgcaat     420
gtcactcatc gaacaattcc atggcgccgc cgccgatgga acggaactca ccgctattta     480
tgctgagcag ccggctgctg atgtggcgtt cgcgctggtc ttcgccggtc acggtcttcc     540
gcgcttcgtg cactgggcc gaccgctcgc ggcgccggga accgtactcg ccgcatacga     600
cgccctgcgg ccgcagcgcg tgtccggcgc gctggacgag accgcctggc caagcatcat     660
gcccacgcaa agcgagtcgt ggataggggc accgcgactg gatatccggc gcgccggcgt     720
aacgccgttc tgtgcattca cggtgaccgg catcgcaatc cgtcaggacg aacgccaagg     780
cgttgacgtg tctgacggcg tggacggtgc cgcgcatacc gtcacgcaac aggtgccggt     840
cgtcaccgtg accgcgtcgg atgccgagca gggcgtggaa ctgtcatgga cggccgaact     900
gttgcccggc ggactgatca gacagcgcac cacgctgcgt aatcttccag ccggtaatct     960
tccgaccggt gacttggaag tcggtaaagt cgaactcggc ttcccgctcc cggcacttgc    1020
cacggagata ctcaccacca ccggccatca tctgcgcgaa cgcagcccgc agcggcagcc    1080
gctgaccgaa ggacgcttcg agaaggtctc gatggcgggg cgcccaggtt ttgacgcctc    1140
tctgttgctt tccgcgggcg agcccggctt cgggttcgag catggcgagg tctattcggt    1200
gcatgtgggc tggagcggca attccgtgct gtcggcagag cgtcagccgt atacgaccgg    1260
tctgattggc ggcggcgagg tgctgctcgg cggcgaggcc acgctcgccc gcggcgaaac    1320
gtacaccacc ccgtggctgt acgggtcgta cggtgacggg ctcaacgagg tggctgcgag    1380
attccatgat tacgtacgct cctgtcaccc ggatctcgcc gtcaagccgc gtccggtgat    1440
tctcaacacg tgggaggccg tgtatttcga ccatgactac gacacgttga aggctctggc    1500
cgataaggcc ggggattccg tgtcgaacg gttcgtggtg gatgacggct ggttcggctc    1560
ccgccgagac tccacatccg ggctcggcga ctggcaaata gcgcaggatg tgtggccgga    1620
cgggccgaag agcctcaagg cgctcgccga ttacgtgcac ggaaaaggca tggagttcgg    1680
cctgtggttc gaaccggaga tggtcaaccc ggattccgac gtggcccgcg cccaccctga    1740
ctgggtgctg cgcccgactg cgaaccgtct gccgatgcag ggacgctcgc agcaagtgct    1800
cgacctgacc aatcccgacg cctaccgata catccatgat tccatcgatg cgctggtcgg    1860
cgagttgggc atcgactaca tcaaatggga ccacaacaaa ttcgtcaccg aggcggtctc    1920
gccacgtacc ggcaggccgg cggtgcacgg gcagacgctc gccgtgtacc ggatgttccg    1980
tgacctcgaa gtcgcgcatc cgggactgga gattgagagt tgcgcatcgg gcggcggcc    2040
tatcgacctg gcatactcg aattcgccag ccgcgtgtgg acgtccgact gcgtggaccc    2100
ggtcgagcgg gccgatattc agcggtacac gtcgctgctc gtgccgccct gcatgatggg    2160
cgagcatgtg ggggcgagtc ctgcacattc cacgcatcgc gccacgagcc aggagatgcg    2220
catggcgatg gcgttcttcg ggcacatggg cgtcgaatgg aatctgctca aggagccgga    2280
cgaggcgttg aacaagctcg gcgaatgggt cgccgaatac aagaggcacc gcgcatggtt    2340
```

```
cgcgatcgac acgtgcgtgc acgccgatat cgccgatccg gccgtccggg tcgacggcat    2400
ggtcaagccg gatcgttccg cggcgttcta ccggttcacg caactgacaa cgtcccagac    2460
tctccctgcg gcgccgattc gcgtgccggg tcttgacccc gatggcacgt accgcataca    2520
gccgttgtgg ctggatctcg atctcgacgg gcttggtctt ggcagcggcc agtcgccgtt    2580
gggctggtgg accaaagacg gcgtgctgat gacgggccgg gcgctgatga cctacgggtt    2640
gcgccctcca tcgctgcatc cggcgcagtc ggtgctgttc accgccattc gccaataagc    2700
cagacggcat cgaacggagc ataacaatgt gccggcggcc cagtcatgga gtcgccggca    2760
cattgcgtca agaacttggg tatcggctc tagtcgttga cgtcggcctt gtagaagttc      2820
acgtaggaac ggctgggggt cgggccgcgc tggccctgat aatgggagcc ggtgcccttg    2880
gagccgtaag ggtgctcggc cggagagctg agctggaaga agcacatctg cccgatcttc    2940
atgccgggcc agagcttgac cggaagcgtc gacacgttgc tcaactccag cgtgatatgc    3000
ccctcgaaac cggggtcgat gaagccggcc gtcaatgtg tgaggatgcc cagacggccc     3060
agcgagcttt tgccttccaa gcgtgccgcc accgtcgcgt cgagcttgac ggtactcccc    3120
acgtcgagc                                                              3129
```

<210> SEQ ID NO 2
<211> LENGTH: 759
<212> TYPE: PRT
<213> ORGANISM: Bifidobacterium bifidum

<400> SEQUENCE: 2

```
Met Ser Leu Ile Glu Gln Phe His Gly Ala Ala Ala Asp Gly Thr Glu
1               5                   10                  15

Leu Thr Ala Ile Tyr Ala Glu Gln Pro Ala Ala Asp Val Ala Phe Ala
            20                  25                  30

Leu Val Phe Ala Gly His Gly Leu Pro Arg Phe Val His Trp Gly Arg
        35                  40                  45

Pro Leu Ala Ala Pro Gly Thr Val Leu Ala Ala Tyr Asp Ala Leu Arg
    50                  55                  60

Pro Gln Arg Val Ser Gly Ala Leu Asp Glu Thr Ala Trp Pro Ser Ile
65                  70                  75                  80

Met Pro Thr Gln Ser Glu Ser Trp Ile Gly Ala Pro Arg Leu Asp Ile
                85                  90                  95

Arg Arg Ala Gly Val Thr Pro Phe Cys Ala Phe Thr Val Thr Gly Ile
            100                 105                 110

Ala Ile Arg Gln Asp Glu Arg Gln Gly Val Asp Val Ser Asp Gly Val
        115                 120                 125

Asp Gly Ala Ala His Thr Val Thr Gln Gln Val Pro Val Val Thr Val
    130                 135                 140

Thr Ala Ser Asp Ala Glu Gln Gly Val Glu Leu Ser Trp Thr Ala Glu
145                 150                 155                 160

Leu Leu Pro Gly Gly Leu Ile Arg Gln Arg Thr Thr Leu Arg Asn Leu
                165                 170                 175

Pro Ala Gly Asn Leu Pro Thr Gly Asp Leu Glu Val Gly Lys Val Glu
            180                 185                 190

Leu Gly Phe Pro Leu Pro Ala Leu Ala Thr Glu Ile Leu Thr Thr Thr
        195                 200                 205

Gly His His Leu Arg Glu Arg Ser Pro Gln Arg Gln Pro Leu Thr Glu
    210                 215                 220

Gly Arg Phe Glu Lys Val Ser Met Ala Gly Arg Pro Gly Phe Asp Ala
```

-continued

```
            225                 230                 235                 240
Ser Leu Leu Leu Ser Ala Gly Glu Pro Gly Phe Gly Phe Glu His Gly
                245                 250                 255
Glu Val Tyr Ser Val His Val Gly Trp Ser Gly Asn Ser Val Leu Ser
                260                 265                 270
Ala Glu Arg Gln Pro Tyr Thr Thr Gly Leu Ile Gly Gly Glu Val
            275                 280                 285
Leu Leu Gly Gly Glu Ala Thr Leu Ala Arg Gly Glu Tyr Thr Thr
            290                 295                 300
Pro Trp Leu Tyr Gly Ser Tyr Gly Asp Gly Leu Asn Glu Val Ala Ala
305                 310                 315                 320
Arg Phe His Asp Tyr Val Arg Ser Cys His Pro Asp Leu Ala Val Lys
                325                 330                 335
Pro Arg Pro Val Ile Leu Asn Thr Trp Glu Ala Val Tyr Phe Asp His
                340                 345                 350
Asp Tyr Asp Thr Leu Lys Ala Leu Ala Asp Lys Ala Gly Asp Ser Gly
                355                 360                 365
Val Glu Arg Phe Val Val Asp Asp Gly Trp Phe Gly Ser Arg Arg Asp
            370                 375                 380
Ser Thr Ser Gly Leu Gly Asp Trp Gln Ile Ala Gln Asp Val Trp Pro
385                 390                 395                 400
Asp Gly Pro Lys Ser Leu Lys Ala Leu Ala Asp Tyr Val His Gly Lys
                405                 410                 415
Gly Met Glu Phe Gly Leu Trp Phe Glu Pro Glu Met Val Asn Pro Asp
                420                 425                 430
Ser Asp Val Ala Arg Ala His Pro Asp Trp Val Leu Arg Pro Thr Ala
                435                 440                 445
Asn Arg Leu Pro Met Gln Gly Arg Ser Gln Gln Val Leu Asp Leu Thr
            450                 455                 460
Asn Pro Asp Ala Tyr Arg Tyr Ile His Asp Ser Ile Asp Ala Leu Val
465                 470                 475                 480
Gly Glu Leu Gly Ile Asp Tyr Ile Lys Trp Asp His Asn Lys Phe Val
                485                 490                 495
Thr Glu Ala Val Ser Pro Arg Thr Gly Arg Pro Ala Val His Gly Gln
                500                 505                 510
Thr Leu Ala Val Tyr Arg Met Phe Arg Asp Leu Glu Val Ala His Pro
            515                 520                 525
Gly Leu Glu Ile Glu Ser Cys Ala Ser Gly Gly Arg Ile Asp Leu
            530                 535                 540
Gly Ile Leu Glu Phe Ala Ser Arg Val Trp Thr Ser Asp Cys Val Asp
545                 550                 555                 560
Pro Val Glu Arg Ala Asp Ile Gln Arg Tyr Thr Ser Leu Leu Val Pro
                565                 570                 575
Pro Cys Met Met Gly His Val Gly Ala Ser Pro Ala His Ser Thr
                580                 585                 590
His Arg Ala Thr Ser Gln Glu Met Arg Met Ala Met Ala Phe Phe Gly
            595                 600                 605
His Met Gly Val Glu Trp Asn Leu Leu Lys Glu Pro Asp Glu Ala Leu
            610                 615                 620
Asn Lys Leu Gly Glu Trp Val Ala Glu Tyr Lys Arg His Arg Ala Trp
625                 630                 635                 640
Phe Ala Ile Asp Thr Cys Val His Ala Asp Ile Ala Asp Pro Ala Val
                645                 650                 655
```

-continued

```
Arg Val Asp Gly Met Val Lys Pro Asp Arg Ser Ala Ala Phe Tyr Arg
            660             665             670

Phe Thr Gln Leu Thr Thr Ser Gln Thr Leu Pro Ala Ala Pro Ile Arg
        675             680             685

Val Pro Gly Leu Asp Pro Asp Gly Thr Tyr Arg Ile Gln Pro Leu Trp
    690             695             700

Leu Asp Leu Asp Leu Asp Gly Leu Gly Leu Gly Ser Gly Gln Ser Pro
705             710             715             720

Leu Gly Trp Trp Thr Lys Asp Gly Val Leu Met Thr Gly Arg Ala Leu
                725             730             735

Met Thr Tyr Gly Leu Arg Pro Pro Ser Leu His Pro Ala Gln Ser Val
            740             745             750

Leu Phe Thr Ala Ile Arg Gln
            755
```

α-GALACTOSIDASE WITH TRANSGALACTOSYLATING ACTIVITY

CROSS-REFERENCE TO RELATED APPLICATION

This application is a National Phase Patent Application of International Application Number PCT/GB2006/004796, filed on Dec. 19, 2006, which claims priority of British Patent Application Number 0525857.9, filed on Dec. 20, 2005.

The present invention relates to a novel α-galactosidase with transgalactosylating activity capable of converting mellibiose to α-galactobiose disaccharides. In particular it relates to an α-galactosidase isolated from a recently discovered strain of *Bifidobacterium bifidum*.

The invention particularly relates to DNA sequences encoding the isolated α-galactosidase enzyme, to the enzyme encoded by such a DNA sequence and to a host cell comprising a DNA sequence or containing a recombinant vector incorporating the DNA sequence. The invention also relates to the use of the enzyme encoded by DNA sequence, or of the host cell containing a DNA sequence or recombinant vector, to produce α-galactobiose.

Bifidobacteria naturally colonise the lower intestinal tract, an environment which is poor in mono and disaccharides since such sugars are preferentially consumed by the host and microbes present in the upper intestinal tract. In order to survive in the lower intestinal tract bifidobacteria produce various kinds of exo- and endoglycosidases in surface bound and/or extracellular forms, by which they can utilise diverse carbohydrates.

Besides hydrolase activity, some enzymes from bifidobacteria show transferase activity. This transglycosylation activity of glycosidases is extensively used for the enzymatic synthesis of various oligosaccharides, which have proven to act as bifidobacteria growth promoting factors.

It is known that members of bifidobacteria produce β-galactosidase enzymes that are involved in the bacterial metabolism of lactose. Moller, P. L. et al in *Appl & Environ. Microbial.*, (2001), 62, (5), 2276-2283 describe the isolation and characterisation of three β-galactosidase genes from a strain of *Bifidobacterium bifidum*. They found that all three β-galactosidases were able to catalyse the formation of beta-linked galactooligosaccharides by transgalactosylation.

It is known that some species of bifidobacteria, but not *B. bifidum* produce α-galactosidases as well as β-galactosidases. α-Galactosidases belong to the group of glycolsyl hydrolases and can be classified into two groups based on their substrate specificity, i.e. one group is specific for small saccharides such as p-nitrophenyl-α-D-galactopyranoside, mellibiose and raffinose, and the other group can liberate galactose from galactomannans such as guar gum, in addition to small substrates.

A strain of *Bifidobacterium bifidum* has been found that is capable of producing a galactosidase enzyme activity that converts lactose to a novel mixture of galactooligosaccharides which unexpectedly contains up to 35% of disaccharides including galabiose (Gal (α 1-6)-Gal). This disaccharide is known (see Paton, J. C. & Paton, A. W. (1998), *Clin. Microbiol. Revs.*, 11, 450-479; Carlsson, K. A. (1989), *Ann. Reviews Biochem.*, 58, 309-350) to be an antiadhesive capable of preventing the adhesion of toxins, e.g. Shiga toxin and pathogens such as *E. coli*, to the wall of the gut.

This strain of *B bifidum* was deposited under accession number NCIMB 41171 at the National Collection of Industrial & Marine Bacteria, Aberdeen, UK on 31 Mar. 2003. It is also described in UK Patent No. 2 412 380.

It has been found that this strain of *B. bifidum* produces an α-galactosidase that is capable of converting mellibiose to α-galactobiose disaccharides.

According to the invention there is provided a DNA sequence which encodes a protein with an amino acid sequence as given in SEQ. ID NO: 2 or hybridises under stringent conditions to the DNA sequence which encodes this protein. The DNA sequence is given in SEQ. ID NO: 1 or may comprise a fragment or degenerative thereof.

The phrase "degenerative" is construed to mean a DNA sequence which is at least 50% homologous to SEQ. ID NO: 1, preferably from 50 to 98% homologous, most preferably from 75 to 95% homologous.

Such a DNA sequence may comprise nucleotide substitutions, additions or deletions which result in less than 60%, preferably less than 45%, more preferably less than 25% change in the amino acid sequence shown in SEQ. ID NO: 2. Nucleotide substitutions may result in conservative amino acid substitutions.

According to a second aspect of the invention there is provided an enzyme encoded by a DNA sequence as defined above. Such an enzyme may comprise the amino acid sequence given in SEQ. ID NO: 2 or a fragment thereof.

According to a third aspect of the invention there is provided a recombinant vector, preferably an expression vector, comprising a DNA sequence as defined above. Such a vector may be incorporated into a host cell such as a bacterial, yeast or fungal cell. Alternatively, the DNA sequence may be incorporated into such a host cell. A suitable host cell may be selected from *Bifidobacterium, Lactococcus, Lactobacillus, Bacillus* for example *Bacillus subtilis* or *Bacillus circulans, Escherichia* and *Aspergillus* for example *Aspergillus niger*.

Using mellibiose as a substrate, the enzyme encoded by the DNA sequence as defined above produces a mixture of oligosaccharides, in particular α-galactobiose disaccharides.

The enzyme or the host cell as described above may be used to produce α-galactobiose disaccharides, which may form part of a product for improving gut health. Such a product may be selected from the group consisting of dairy products (for example liquid milk, dried milk powder such as whole milk powder, skimmed milk powder, fat filled milk powders, whey powders, baby milks, baby formula, ice cream, yoghurt, cheese, fermented dairy products), beverages such as fruit juice, infant foods, cereals, bread, biscuits, confectionery, cakes, food supplements, dietary supplements, probiotic comestible products, prebiotic comestible products, animal feeds, poultry feeds or indeed any other food or beverage.

Alternatively, the disaccharides so produced may be used for the preparation of a medicament for example in tablet or capsule form for preventing the adhesion of pathogens or toxins produced by pathogens to the gut wall. The medicament may be administered to a patient, for example following a course of antibiotic treatment, which often alters or even destroys the normal healthy gut flora.

According to yet a further aspect of the invention there is provided a process for producing an enzyme as defined above which comprises culturing a host cell as defined above in a suitable culture medium under conditions permitting expression of the enzyme and recovering the resulting enzyme or enzyme products from the culture.

The invention is also directed to a process for producing the galactobiose disaccharides which comprises contacting the enzyme as defined above or a host cell as defined above with a mellibiose-containing material under conditions that lead to the formation of the disaccharides.

Suitable mellibiose containing material may be selected from commercially available mellibiose, raffinose, stachyose or as an extract of soybeans.

BRIEF DESCRIPTION OF THE DRAWINGS

FIG. 1 shows the nucleotide sequence (SEQ. ID NO: 1) of *Bifidobacterium bifidum* α-galactosidase with the start and stop codon indicated in bold letters;

FIG. 2 shows the nucleotide sequence of FIG. 1 with the amino acid sequence (SEQ. ID NO: 2) of the enzyme;

FIG. 3 shows the first 540 amino acids of the amino acid sequence (SEQ. ID NO: 2) of FIG. 2;

Figure 4:
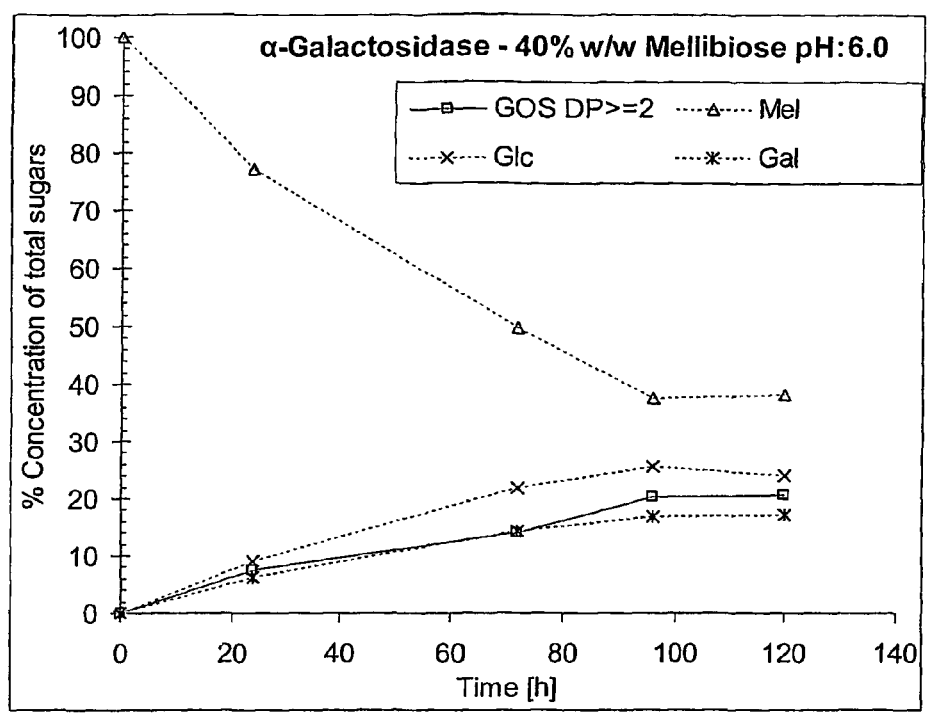
FIG. 4 is a graph showing the time course reaction during α-galactooligosaccharide synthesis with the α-galactosidase and 40% (w/w) mellibiose in 0.1M phosphate buffer at pH 6.0 as substrate.

Genomic DNA was isolated from the *Bifidobacterium bifidum* strain (NCIMB 41171) using the method of Lawson et al. (1989) *Fems Microbiol* Letters, 65, (1-2), 41-45. The DNA was digested with restriction enzymes and fragments having a maximum size of 15 kbp were ligated with pBluescript KS(+) vector. *E. coli* cells were transformed with a vector containing insertions consisting of PstI digested chromosomal DNA from the *B. bifidum*. Clones with α-galactosidase activity were selected on Luria Bertani agar plates containing p-nitrophenyl α-D-galactopyronoside and isopropyl-β-D-thiogalactoside (IPTG). Two α-galactosidase positive clones (pMelA1 and pMelA2) were identified.

The two positive clones were digested with EcroR1, PstI and Bam HI and showed a similar restriction pattern indicating that both contained the same inserted DNA fragment. DNA sequencing of the inserted DNA fragment MelA1 was performed using the dideoxy chain-termination method of Sanger (Russel P., 2062 iGenetics, Pearson Education, Inc., San Francisco, 187-189) using the BigDye Terminator V.3.O cycle sequencing kit (Applied Biosystems, USA). The DNA sequence of MelA1 is shown in FIG. 1 (SEQ. ID NO: 1).

The open reading frame (ORF) was located by using the ORF finder from NCBI (National Center of Biotechnology Information). The bacterial genetic code was used and the frame length was determined to be 300 bp. The nucleotide sequence of FIG. 1 was translated in all six possible reading frames and one open reading frame of 759 amino acids encoding a putative α-galactosidase was identified. The translation is shown in FIG. 2 (SEQ. ID NO: 2).

The present invention will be further described by way of reference to the following examples.

EXAMPLE 1

Materials and Methods

All chemicals and media preparations used throughout this study were obtained from Sigma (Dorset, UK), Invitrogen (Paisley, UK), Oxoid (Basingstoke, UK), Qiagen (West Sussex, UK) and Promega (Southampton, UK).

Bacterial Strains

The *Bifidobacterium bifidum* strain (NCIMB 41171) was maintained on cryogenic beads in Microbank tubes at −70° C. For later experiments, the strain was revived on Wilkinson Chalgren (WC) agar (Oxoid, UK) and TPY medium (trypticase phytone yeast extract medium) and grown anaerobically ($CO_2$ and $N_2$ composition 80% and 20% respectively) at 37° C. for 48 hours. The colony morphology and the absence of contamination were tested by gram staining.

*E. coli* Strains

*Escherichia coli* strains RA11r and DH5a used in this study were commonly incubated under aerobic conditions at 37° C. in Luria Bertani (LB) agar or broth (Sambrook J. and Russell, W. D., (2001) Molecular Cloning: A Laboratory Manual. Cold Spring Harbour Laboratory Press, New York) and when necessary was supplemented with antibiotics (100 μg/ml ampicillin and/or 15 μg/ml chloramphenicol) and 40 μl of 2% X-α-galactopyranoside (X-α-Gal), 7 μl of 20% (isopropyl-β-D-thiogalactoside) IPTG which were applied on the surface of a pre-made 90 mm agar plate.

The α-galactosidase deficient strain *E. coli* RA11r (Hanatani et al, 1983, *J. Biol. Chem.*, 259, (3), 1807-1812) (genotype: $melA^-B^+$, $recA^-$, $lacZ^-Y^-$) is a derivative of *E. coli* K12 and was used in expression experiments. *E. coli* DH5a strain (Invitrogen, Paisley, UK) (genotype: $F^-\phi 80lacZ\Delta M$ Δ(lac-ZYA-argF)U169 recA1 endA1 hsdR17($r_k^-$, $m_k^-$) phoA supE44 thi-1 gyrA96 relA1λ$^-$) is an α-galactosidase positive strain and was used for all other genetic manipulations.

The choice of *E. coli* strain RA11r, for expression experiments, was done according to its genotype. This strain does not encode an active α-galactosidase due to melA mutation on its chromosomal DNA. However, this strain has an active melibiose transporter which is necessary for the transport of sugars (melibiose) into the cytoplasma and hence the metabolism of them by active α-galactosidases. It was not known whether the *Bifidobacterium bifidum* α-galactosidase was expressed intracellularly or extracellularly. So the existence of an active melibiose transporter was essential for the identification of the α-gal positive clones and hence the isolation of α-galactosidase encoding genes.

Moreover this strain is a recA mutant which minimises recombination of introduced DNA with host DNA, thus increasing the stability of inserts.

Genomic DNA Extraction from *Bifidobacterium bifidum*

Genomic DNA was isolated from the *Bifidobacterium bifidum* strain (NCIMB 41171) by using the method of Lawson et al. (1989).

According to this method, cells were harvested from plates in 0.5 ml of TES buffer in 1.5 ml ependorfs. 10 μl of lysozyme/mutanolysin mixture (4:1, lysozyme 10 mg/ml; mutanolysin 1 mg/ml) were added and the mixture was then mixed and incubated for 30 minutes at 37° C. The cells were then treated with 10 μl of proteinase K (at 20 mg/ml) and 10 μl RNase (10 mg/ml), mixed and incubated for 1 hour at 65° C. After incubation, 100 μl of 10% SDS was added and the cell lysates were gently mixed by inversion and incubated for a further 15 minutes at 65° C., followed by addition of 0.62 ml of phenol/chloroform and mixed by inversion until an emulsion formed. The cell lysate was centrifuged at 6,500 rpm for 10 minutes and the upper aqueous layer was transferred to a clean ependorf using a flamed, wide bore blue pipette tip. The extraction (deproteinazation step) was repeated until cell debris was removed completely. The DNA was precipitated by the addition of 1 ml ice-cold ethanol followed by incubation for at least 30 minutes on ice or stored overnight in a −20° C. freezer. The genomic DNA was recovered by centrifugation at 13,000 rpm for 5 minutes and after drying it was re-suspended in 50 μl of sterile 10 mM Tris-Cl pH 8.

The extracted DNA was analysed by gel electrophoresis and the concentration measured at 260 nm. It was stored in −20° C. or −70° C. for prolonged periods of time and multiple thawing and freezing was avoided in order to reduce the possibility of degradation.

Vector DNA Preparation

The vector used throughout this study was the pBluescript KS(+) (Stratagene, North Torrey Pines Road). This cloning vehicle was chosen because of the lac promoter which pBluescript KS (+) encodes which is necessary for the transcription initiation of genes which lack their own promoter.

The vector was digested with the following restriction enzymes: PstI, BamHI and EcoRI according to the manufacturer's instructions using a tenfold excess of enzyme over DNA (enzyme units:µgr DNA equal to ten units of enzyme per one µgr of plasmid DNA or ten enzyme units per 0.5 pmol of plasmid DNA). After enzyme heat inactivation (20 min at 65° C.) the restriction patterns were analysed by horizontal gel electrophoresis analysis.

The vectors were further dephosphorylated with calf intestinal alkaline phosphatase CIAP (Promega, Southampton, UK) according to the manufacturer's instructions. The efficiency of the treatment was tested by self-ligation of the vector (with Bacteriophage T4 DNA ligase according to manufacturer's instructions) following transformation into DH5a cells.

The presence of a single fragment in the gel indicated the complete vector digestion and the single restriction digestion of it. The sufficient digestion of the vector was tested also by transforming unligated molecules into competent *E. coli* DH5a cells. The number of formed colonies on LB agar plates supplemented with ampicillin (100 µgr/ml) was an indicator of the undigested molecules and the expected background during the subsequent experiments.

Genomic DNA Library Construction

Genomic DNA was partially digested with three restriction enzymes that recognise frequently occurring hexa-nucleotide sequences within prokaryotic DNA. EcoRI, BamHI and PstI are type II restriction endonucleases specifically recognizing the sequences 5'G/AATTC'3, 5'G/GATCC'3 and 5'CTGCA/G'3 respectively, and make double-strand breaks within these sequences generating 5' overhangs of four nucleotides, AATT GATC for EcoRI and BamHI respectively, and 3' overhangs, ACGT for PstI.

All these enzymes were active and able to cleave DNA only in the presence of divalent magnesium ions. These ions were the only required cofactor.

Restriction Digestion of DNA.

All restriction digestions of the genomic DNA samples were incubated for 2 hours at 37° C. and finally heat inactivated at 65° C. for 20 minutes. The reactions were then cooled at room temperature and the appropriate amount of loading buffer was added, followed by gentle mixing with a sealed glass capillary. The solutions then were loaded into wells of a 0.8% agarose gel (power supply 4-5 volts/cm for 14-16 hours) and the size of the digested DNA was estimated with that of 1 kbp DNA standards (Promega, UK) (Sambrook J. Molecular Cloning: A Laboratory Manual (2002)).

Purification of the Fragments Generated after Restriction Digestion.

Fragment purification from the reaction mixtures and the agarose gels was done by using the QIAEX gel extraction kit from Qiagen (West Sussex, UK). Protocols are described with details in the manufacturer's manual.

DNA Ligation and Transformation

After purification of the DNA fragments with the Qiaex gel extraction kit, they were ligated with CIAP-treated pBluescript KS (+) vector. For ligation, appropriate amounts of DNA were transferred to sterile 0.5 ml microfuge tubes as shown in Table 1.

TABLE 1

Ligation mixtures.

| Tube | DNA |
|---|---|
| A | Vector (15 fmoles [~29.7 ng]) |
| B | Vector (15 fmoles ~29.7 ng DNA) plus insert (foreign 15 fmoles ~69.3 ng) |
| C | pUC control (0.056 fmoles [~100 pg]) |

The molar ratio of plasmid DNA vector to insert DNA fragment should be ~1:1 in the ligation reaction. The final DNA concentration should be ~10 ng/µl.
Tube A shows the number of self-ligated vector DNA which must be subtracted from the total number of transformants after transformation. Tube B shows the ligation of the vector with the DNA fragments and tube C shows the control in order that the transformation efficiency to be calculated.

Before each ligation the DNA fragments were warmed at 45° C. for 5 minutes to melt any cohesive termini that reannealed during fragment preparation. A molar ratio of vector: insert DNA of 1:1 was chosen for all ligation reactions and the reaction assembly was done according to Promega's instructions.

To tubes A and B 1.0 µl of 10× ligation buffer and 0.5 Weiss units of T4 DNA ligase (Promega, UK) were added and the ligation volume was adjusted to 10 µl with molecular biology grade water. To tubes C 1.0 µl of 10× ligation buffer were added and the ligation volume was adjusted to 10 µl with molecular biology grade water.

DNA fragments were added to the tubes together with the water and then warmed to 45° C. for 5 minutes to melt any cohesive termini that were reannealed during preparation. The DNA was chilled to 0° C. before the remainder of the ligation reagents were added and the reaction mixtures were incubated overnight at 16° C. (Sambrook and Russell, 2001).

After ethanol precipitation and purification of the ligated fragments (in order to remove the ligation mixture which cause reduction of the transformation efficiency) transformations were performed according to Hanahan instructions. ~50 ng of ligated DNA in 5 µl solution was added to 100 µl of competent *E. coli* RA11r cells. After heat treatment and expression of the ampicillin resistance gene the cells were spreaded over the surface of LB plates containing ampicillin (100 µr/ml), X-α-Gal (40 µl of 2% X-α-Gal) and IPTG (7 µl of 20% IPTG).

The number of transformants from each ligation reaction was measured. The number of transformants commonly obtained from tube C was $2 \times 10^5$-$1 \times 10^6$ cfu/µg whereas from tube A was 500-600 cfu/µg. The number of transformants in tube A was an indication of the efficient treatment of the vector DNA. The number of transformants in tube B was in a range from $2$-$4 \times 10^4$ cfu/µg.

Number of Transformants

Ligation mixtures with PstI chromosomal DNA gave rise to two α-galactosidase positive clones (pMelA1 and pMelA2) out of approximately 2500 screened transformants, whereas with EcoRI and BamHI-treated chromosomal DNA did not give any positive clone out of approximately 4000 total screened transformants.

Positive Clone Digestion

The two PstI positive clones were digested with EcroRI, PstI, BamHI, HindIII, SmaI, and KpnI restriction enzymes. Restriction enzymes EcroRI, PstI and BamHI showed similar restriction pattern, one fragment of ~5 kbp (gene of interest) and one ~3 kbp (plasmid DNA) indicating that these enzymes were cut at the same positions. HindIII gave a fragment at 6.5 kbp and a fragment at 1.5 kbp whereas enzymes SmaI and KpnI gave one fragment with size ~8 kbp indicating that they were cut at only one position. The similar restriction patterns for both plasmids were an indication that both contain the same DNA fragment insert.

DNA Sequencing

DNA sequencing was performed with the dideoxy chain-termination method of Sanger by using the BigDye Terminator v.3.0 cycle sequencing kit (Applied Biosystems, USA) and analysed with the ABI Prism 3100, a fluorescence-based DNA analysis system incorporating capillary electrophoresis.

The 5'- and 3'-ends of the inserted DNA fragments were sequenced with vector specific primers. The inserts were further sequenced by using the Genome Priming System (GPS-1) (New England Biolabs, Uk). GPS-1 is a TN7 transposon-based in vitro system which uses TnsABC Transposase to insert Transposon randomly into the DNA target. The donor:target DNA mass ratio of 1:4 was used according to the manufacturer instructions. The number of isolated plasmids for sequencing after insertion of the Transprimer into the target plasmid was 25. This number was calculated according to the manufacturer instructions and it assumes a 5-fold depth of coverage.

Unique priming sites on both ends of the Transprimer element allowed the sequencing of both strands of the target DNA at the position of the insertion.

The sequencing reaction mix contained approximately 400-600 ng plasmid DNA, 3.2 pmol of primer solution and 4 µl of BigDye Terminator solution.

Open Reading Frame Identification

The open reading frame (ORF) was located by using the ORF finder from NCBI. The bacterial genetic code was used and the frame length was determined to be 300 bp. The nucleotide sequence was translated in all six possible frames and one open reading frame of 759 amino acids encoding a putative α-galactosidase was identified (The translation is shown in FIG. 2). The start and stop codon was confirmed.

The Bifidobacterium α-galactosidase gene on plasmid pMelA1 was expressed in E. coli under growth conditions which would normally repress expression from the inducible E. coli lacZ promoter located in the flanking region of the cloning vector. This observation indicated that endogenous, internal bifidobacterial sequences upstream of the α-galactosidase gene may serve as a transcription initiation signal in E. coli.

The transcription start is indicated with bold italic letter. The above results indicate that the gene is controlled from its own promoter for transcription.

EXAMPLE 2

Synthesis with the α-Galactosidase Cloned Enzyme Isolated from *Bifidobacterium bifidum* NCIMB 41171 in *E. coli* Host (Strain RA11)

The following described synthesis, unless otherwise stated, was performed with the whole *E. coli* RA11 host cells after treatment of the *E. coli* biomass (collected by centrifugation at 10,000 g) with toluene at a concentration of 2000 ppm in order to increase cell permeability and also to render the cells non-viable by destroying their cytoplasmic membrane. The E-coli biomass was prepared as described in. Example 1 under "*E coli* strains".

Synthesis with Cloned Enzyme

Synthesis with α-galactosidase was performed at a substrate concentration of 40% (w/w) initial mellibiose concentration. The synthesis solution was prepared in 0.1 M phosphate buffer at pH 6.0. Synthesis was performed at 40° C. in shaking waterbath at 150 rpm. The pH optimum for the specific enzyme was chosen based on activity measurements (using p-nitrophenyl-α-D-galactopyranoside as substrate) of a specific enzymatic preparation at varying pH values.

For α-galactosidase synthesis 2 ml of an *E. coli* RA11 cell suspension (with an activity of 0.3 U/ml) were centrifuged (at 10,000 g) to collect the biomass and the supernatant was discarded. This biomass was re-suspended with 1 g of 40% (w/w) mellibiose substrate solution in order to perform the synthesis.

Figure 5:
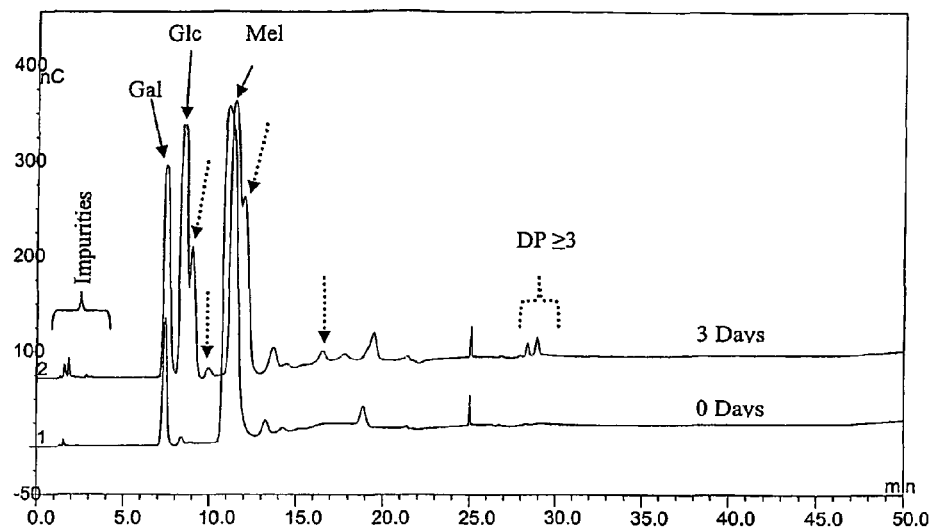
FIG. 5 shows a high performance anion exchange chromatogram of the α-galactooligosaccharide mixture synthesized by the α-galactosidase from *B. bifidum* NCIMB 41171 using 40% (w/w) mellibiose in 0.1 M phosphate buffer at pH 6.0 as substrate. (Glc=glucose, Gal=galactose, Mel=mellibiose, DP=degree of polymerization). The dashed arrows denote the galactooligosaccharide products.

The concentrations of the different sugars present in the mixture during synthesis are shown in FIG. 4. High performance anion exchange chromatography coupled with pulsed amperometric detection (HPAEC-PAD) chromatograms of galactooligosaccharide mixtures synthesized by the α-galactosidase cloned from *B. bifidum* NCIMB 41171 are shown in FIG. 5. The galactooligosaccharide mixture sugar concentrations at the optimum synthesis time point are shown in table 1.

TABLE 1

Carbohydrate composition of α-galactooligosaccharide synthesis at 40% (w/w) initial mellibiose concentration at the time point where maximum oligosaccharide concentration was observed.

| Synthesis Init. Subst. % (w/w) | GOS DP ≧ 3 | GOS DP = 2 | Mel | Glc | Gal |
|---|---|---|---|---|---|
| | | Concentration (% of total sugars) | | | |
| 40 | 13.93 | 6.61 | 38.06 | 24.1 | 17.29 |

Mel: Mellibiose,
Glc: glucose,
Gal: galactose,
DP: degree of polymerisation

The invention claimed is:

1. An isolated enzyme encoded by a DNA sequence as set forth in SEQ. ID. NO: 1.

2. An isolated enzyme comprising an amino acid sequence as set forth in SEQ. ID. NO: 2.

3. A method of producing a product for improving gut health, comprising:
    contacting the enzyme of claim 1 or 2 with a solution of mellibiose to form α-galactobiose disaccharides;
    contacting the α-galactobiose disaccharides with a product selected from the group consisting of diary products, liquid milk, dried milk powder, baby milks, baby formula, ice cream, yoghurt, cheese, fermented diary products, beverages, fruit juice, infant foods, cereals, bread, biscuits, confectionary, cakes, food supplements, dietary supplements, probiotic comestible products, prebiotic comestible products, animal feeds, poultry feeds, and medicaments.

4. A process for producing a disaccharide comprising contacting the enzyme of claim 1 or 2 with a solution of mellibiose.

* * * * *

UNITED STATES PATENT AND TRADEMARK OFFICE
CERTIFICATE OF CORRECTION

| | |
|---|---|
| PATENT NO. | : 8,058,047 B2 |
| APPLICATION NO. | : 12/086834 |
| DATED | : November 15, 2011 |
| INVENTOR(S) | : Georgios Tzortzis et al. |

It is certified that error appears in the above-identified patent and that said Letters Patent is hereby corrected as shown below:

In the Specification

| | |
|---|---|
| Column 3, line 42. | Delete "2062" |
| | Insert -- 2002 -- |
| Column 6, Table 1 Description, line 5. | Delete "that" |
| | Insert -- for -- |
| Column 6, line 39. | Delete "cause" |
| | Insert -- causes -- |
| Column 6, line 44. | Delete "spreaded" |
| | Insert -- spread -- |

In the Claims

| | |
|---|---|
| Column 15, Claim 3, line 31. | Delete "diary" |
| | Insert -- dairy -- |
| Column 16, Claim 3, line 21. | Delete "diary" |
| | Insert -- dairy -- |

Signed and Sealed this
Sixteenth Day of October, 2012

David J. Kappos
*Director of the United States Patent and Trademark Office*